United States Patent [19]

McAndrew et al.

[11] Patent Number: 5,742,399
[45] Date of Patent: Apr. 21, 1998

[54] METHOD FOR STABILIZING THE WAVELENGTH IN A LASER SPECTROMETER SYSTEM

[75] Inventors: James McAndrew, Lockport; Ronald S. Inman, Lyons, both of Ill.

[73] Assignee: American Air Liquide, Inc., Walnut Creek, Calif.

[21] Appl. No.: 711,780

[22] Filed: Sep. 10, 1996

Related U.S. Application Data

[63] Provisional application No. 60/005,013, Oct. 10, 1995, and a continuation-in-part of Ser. No. 634,448, Apr. 18, 1996, abandoned.

[51] Int. Cl.[6] .................................................. G01N 21/31
[52] U.S. Cl. ............................................................ 356/437
[58] Field of Search ............................................. 356/437

[56] References Cited

U.S. PATENT DOCUMENTS

| | | |
|---|---|---|
| 3,524,066 | 8/1970 | Blakkan. |
| 3,994,603 | 11/1976 | Paschedag. |
| 4,812,665 | 3/1989 | Puumalainen et al.. |
| 4,934,816 | 6/1990 | Silver et al. ........................ 356/437 X |
| 4,937,461 | 6/1990 | Traina ................................. 356/437 X |
| 4,990,780 | 2/1991 | Lee et al.. |
| 5,024,526 | 6/1991 | von Redwitz. |
| 5,045,703 | 9/1991 | Wieboldt et al.. |
| 5,065,025 | 11/1991 | Doyle. |
| 5,173,749 | 12/1992 | Tell et al.. |
| 5,220,402 | 6/1993 | Harvey ................................... 356/246 |
| 5,241,851 | 9/1993 | Tapp et al.. |
| 5,294,289 | 3/1994 | Heinz et al.. |
| 5,331,409 | 7/1994 | Thurtell et al.. |
| 5,352,902 | 10/1994 | Aoki ....................................... 250/575 |
| 5,453,621 | 9/1995 | Wong. |
| 5,459,574 | 10/1995 | Lee et al.. |
| 5,485,276 | 1/1996 | Bien et al.. |
| 5,517,314 | 5/1996 | Wallin. |
| 5,536,359 | 7/1996 | Kawada et al.. |
| 5,550,636 | 8/1996 | Hagans et al.. |
| 5,561,527 | 10/1996 | Krone-Schmidt et al.. |
| 5,578,829 | 11/1996 | Talasek et al.. |

FOREIGN PATENT DOCUMENTS

| | | |
|---|---|---|
| 0015170 | 9/1980 | European Pat. Off.. |
| 0647845 | 4/1995 | European Pat. Off.. |
| 0 706 042 | 4/1996 | European Pat. Off.. |
| 0738887 | 4/1996 | European Pat. Off.. |
| 3633931 | 4/1988 | Germany. |
| 4214840 | 11/1993 | Germany. |
| 2075213 | 11/1981 | United Kingdom. |
| 2165640 | 4/1986 | United Kingdom. |
| WO90/00732 | 1/1990 | WIPO. |
| WO94/24528 | 10/1994 | WIPO. |

OTHER PUBLICATIONS

Atkinson, "High Sensitivity Detection of Water Via Intracavity Laser Spectroscopy," Microcontamination Conference Proceedings, pp. 98–111 (1994).

Borden, "Monitoring Vacuum Process Equipment: In Situ Monitors—Design and Specification," Microcontamination, vol. 9, No. 1, pp. 43–47 (1991).

Davies et al, "Infrared Laser Diagnostics in Methane Chemical–Vapor–Deposition Plasmas," Journal of Applied Physics, vol. 71, No. 12, Jun. 15, 1992, pp. 6125–6135.

Feher et al, "Tunable Diode Laser Monitoring of Atmospheric Trace Gas Constituents," Spectrochimica Acta, A 51, pp. 1579–1599 (1995).

Fried et al, "Application of Tunable Diode Laser Absorption for Trace Stratospheric Measurements of HCL: Laboratory Results," Applied Optics, vol. 23, No. 11, Jun. 1984, pp. 1867–1880.

Grisar et al, "Fast Sampling Devices for Dynamic Exhaust Gas Analysis," Proceedings of the 24th ISATA International Symposium on Automotive Technology and Automation, 20 May 1991, pp. 283–287.

Herriott et al., "Folded Optical Delay Lines", Applied Optics, vol. 4, No. 8, pp. 883–889 (Aug. 1965).

Inman et al, "Application of Tunable Diode Laser Absorption Spectroscopy to Trace Moisture Measurements in Gases," Analytical Chemistry, vol. 66, No. 15, pp. 2471–2479.

(List continued on next page.)

Primary Examiner—Vincent P. McGraw
Attorney, Agent, or Firm—Burns, Doane, Swecker & Mathis, L.L.P.

[57] ABSTRACT

Provided is a novel method for wavelength stabilization in a laser spectrometer useful in spectroscopic measurement. According to the method, an initial scan is performed which comprises applying a current or voltage signal to a laser. In the scan, a current or voltage signal value is increased incrementally from a minimum signal value to a maximum signal value over a predetermined total number of signal values. The minimum and maximum signal values are selected such that an absorption feature of a species to be measured falls within the scan bounded by the minimum and the maximum signal values. The relative position of the absorption feature is determined with respect to the applied signal values in the previous scan by analysis of detector outputs corresponding to the signal values in the previous scan. An absorption value corresponding to the absorption feature is determined, and the concentration of the species to be measured can optionally be calculated. A new current or voltage signal scan is defined by resetting the signal values from the previous scan, so as to set the absorption feature in the new current or voltage scan in the same relative position with respect to the applied signal values as in the previous scan. An additional scan is performed, and the steps can be repeated until completion of the spectroscopic measurement. The inventive method allows for automatic correction and stabilization of wavelength in real time without the need for significant computation beyond what is typically required for determining the concentration of the species of interest from the spectroscopic data. Particular applicability is found in tunable diode laser absorption spectroscopy (TDLAS).

24 Claims, No Drawings

OTHER PUBLICATIONS

Jasinski et al, "Detection of SiH$_2$ in Silane and Disilane Glow Discharges by Frequency Modulation Absorption Spectroscopy," *Applied Physics Letters*, vol. 44, No. 12, Jun. 15, 1984, pp. 1155–1157.

Lichtman, "Residual Gas Analysis: Past, Present and Future," J. Vac. Sci. Technol. A8(3), pp. 2810–2813 (1990).

Mitsui et al., "Development of New APIMS for the Detection of Trace Impurities in Special Gases", Proceedings of the 40th Annual Technical Meeting of the IES, Chicago, pp. 246–253 (1994).

Mucha et al., "Infrared Diode Laser Determination of Trace Moisture In Gases", ISA Transactions, vol. 25, No. 3, pp. 25–30 (1986).

Podolske et al, "Airborne Tunable Diode Laser Spectrometer for Trace-Gas Measurement in the Lower Stratosphere," *Applied Optics*, vol. 32, No. 27, pp. 5324–5333.

Pokrowsky et al, "Sensitive Detection of Hydrogen Chloride by Derivative Spectroscopy with a Diode Laser," *Optical Engineering*, vol. 23, No. 1 (1984), pp. 088–091.

Riris et al, "Design of an Open Path Near-Infrared Diode Laser Sensor: Application to Oxygen, Water, and Carbon Dioxide Vapor Detection," *Applied Optics*, vol. 33, No. 30, Oct. 20, 1994, pp. 7059–7066.

Smoak, Jr. et al, "Gas Control Improves EPI Yield", Semiconductor Int'l., pp. 87–92 (1990).

Staab, "Industrielle Gasanalyse Industrial Gas Analysis," *Technisches Messen*, vol. 61, No. 3, Mar. 1, 1994, pp. 133–137.

White, "Long Optical Paths of Large Aperture", J. Opt. Soc. Am., vol. 32 (1942), pp. 285–288.

Wilson, "Modulation Broadening of NMR and ESR Line Shapes", J. App. Phys., vol. 34, No. 11, pp. 3276–3285 (1963).

T. A. Hu et al, "Improved Multipass Optics for Diode Laser Spectroscopy", Review of Scientific Instruments, vol. 64, No. 12, Dec. 1993, pp. 3380–3383.

Patent Abstracts of Japan, vol. 6, No. 59, JP 57–1953, Jan. 1982.

Fried et al., "Versatile Integrated Tunable Diode Laser System for High Precision: Application for Ambient Measurements of OCS", Applied Optics, vol. 30, No. 15, May 20, 1991; pp. 1916–1932.

May, "Correlation–Based Technique for Automated Tunable Diode Laser Scan Stabilization", Rev. Sci. Instrum., vol. 63, No. 5, May 1992, pp. 2922–2926.

Eng et al., "Tunable diode Laser Spectroscopy: An Invited Review", Optical Engineering, Nov./Dec. 1980, vol. 19, No. 6; pp. 945–960.

Lundqvist et al., "Measurements of Pressure–Broadening Coefficients of NO and O$_3$ Using a Computerized Tunable Diode Laser Spectrometer", Applied Optics, vol. 21, No. 17, Sep. 1, 1982, pp. 3109–3113.

Ahlberg et al., "IR–Laser Spectroscopy for Measurement Applications in the Industrial Environment", TR 85170; Dec. 1985.

Höjer et al., "Measurements of Electric Field Strength In Gas Insulated High–Voltage Components Using Infrared Diode Laser Absorption Spectroscopy", Applied Optics, vol. 25, No. 17, Sep. 1, 1986, pp. 2984–2987.

Cassidy; "Trace Gas Detection Using 1.3μm InGaAsP Diode Laser Transmitter Modules", Applied Optics, vol. 27, No. 3, Feb. 1, 1988, pp. 610–614.

May, "Computer Processing of Tunable Diode Laser Spectra", Applied Spectroscopy, vol. 43, No. 5, 1989, pp. 834–839.

May et al., "Data Processing and Calibration for Tunable Diode Laser Harmonic Absorption Spectrometers", J. Quant. Spectrosc. Radiat. Transfer, vol. 49, No. 4, 1993, pp. 335–347.

Lowenstein, "Diode Laser Harmonic Spectroscopy Applied to In Situ Measurements of Atmospheric Trace Molecules", Journal of Quantitative Spectroscopy and Radiative Transfer, vol. 40, No. 3, pp. 249–256 (1988).

Webster et al., "Aircraft (ER–2) Laser Infrared Absorption Spectrometer (Alias) for In–situ Statospheric Measurements of HCl, N$_2$O, CH$_4$, NO$_2$, and HNO$_3$", Applied Optics, vol. 33, No. 3, pp. 454–472 (Jan. 20, 1994).

METHOD FOR STABILIZING THE WAVELENGTH IN A LASER SPECTROMETER SYSTEM

CROSS REFERENCE TO RELATED APPLICATIONS

This application is a Continuation-in-Part of application Ser. No. 08/634,448, filed Apr. 18, 1996, now abandoned, and this application claims the benefit of U.S. Provisional application No. 60/005,013 filed Oct. 10, 1995.

BACKGROUND OF THE INVENTION

1. Field of the Invention

The present invention relates to a novel method for stabilizing the wavelength in a laser spectrometer system, and more particularly, to stabilizing the wavelength in a tunable diode laser absorption spectroscopy (TDLAS) system.

2. Description of the Related Art

Tunable diode laser absorption spectroscopy (TDLAS) is a technique having considerable flexibility and sensitivity, which has become widely used in environmental monitoring, spectroscopy, chemical kinetics and the like. TDLAS lends itself to the detection and measurement of concentrations of gas phase molecules.

According to the TDLAS technique, a diode laser is used as a radiation source, and is tuned to emit light at a particular wavelength which corresponds to a characteristic of a molecular species desired to be detected in a sample. Among the molecular species which can be measured, water vapor is of particular interest.

The light beam generated by the diode laser is transmitted into a sample region containing the molecular species of interest. The fraction of the light emitted by the laser diode which is transmitted through the sample is measured by a detector, such as a photodiode. The intensity of light reaching the detector is given by Beer's Law:

$$I = I_o \cdot e^{-\alpha l c P}$$

where $I_o$ is the intensity of the incident radiation, $\alpha$ is the absorptivity, $l$ is the pathlength through the sample, $c$ is the concentration of the impurity in the sample (by volume), and $P$ is the total pressure of the sample. The signal generated by the detector may be used to determine the concentration of the molecular species of interest in the sample.

Tuning of the wavelength of the light emitted by the diode laser can be effected by varying the temperature of the diode and/or the current applied thereto. Wavelength tuning has a very high resolution, and the characteristic shape of absorption features, i.e., the variation in light absorption about the center frequency, is easily observed.

Among the factors which control the precision of gas measurements obtained by TDLAS is the extent of wavelength drifting of the light emitted by the diode laser. Control of the wavelength is extremely difficult, and diode properties may drift even if the diode is precisely maintained at a constant temperature and current. Thus, even at constant diode temperature and applied current, the wavelength of the emitted light drifts slowly with time.

Two known methods for dealing with the problem of wavelength drift in diode lasers are known. In the first method, a feedback signal is supplied to the laser diode. This feedback signal tends to lock the emitted light to a specific wavelength. To control the diode laser to emit light having a wavelength corresponding to a characteristic absorption of a molecular species of interest, suitable electronics may be used to generate a signal corresponding to the first or third derivative of the absorption signal. Feeding this derivative signal back to the diode will tend to lock the laser wavelength to the center wavelength of the absorption feature.

However, this first approach is disadvantageous. Because the laser emission is locked to a single wavelength, the only information obtained relates to the light transmitted at that specific wavelength. It is highly desirable that information related to light transmission at neighboring wavelengths be obtained. With such additional information, the shape/profile of the absorption feature can be determined.

Additionally, the information from neighboring wavelengths can be used as a diagnostic check of the spectrometer itself to ensure proper operation thereof. For example, the neighboring wavelengths can be used to ensure the absence of interference due to absorption at the neighboring wavelengths.

The feedback technique generally works only for absorption measurements having a relatively high signal to noise ratio, which means that either the molecule of interest must be in the sample at a sufficient concentration, or a reference light path which passes through a reference sample of the molecule of interest at a sufficient concentration must be provided.

In a second solution to the problem of wavelength drift, the laser wavelength is rapidly and repetitively varied, i.e., scanned, over a region which includes the wavelength at which absorption occurs, as well as a portion of the surrounding wavelength. Data from subsequent scans may be analyzed individually or averaged, depending on the time-resolution required. By averaging the values, improved signal-to-noise ration may be obtained. According to this scanning technique, information pertaining to the shape of the absorption as well as other diagnostic information relating to spectrometer operation can be obtained.

It is further known to automate the wavelength scanning technique, wherein the current applied to the diode laser is computer controlled. In this case, the diode laser current scan range is entered into the computer software. Since wavelength of the light is a function of the current applied to the diode laser, the wavelength of the light is scanned as the current is scanned. Automated wavelength scanning is described in detail in R. D. May, Applied Spectroscopy Vol. 43(5), pp. 834–839 (1989); R. D. May and C. R. Webster, Journal of Quantitative Spectroscopy and Radiative Transfer, Vol. 49(4).

For each current (or wavelength) value, an absorption signal is generated by the detector. From the absorption signal at each current and wavelength, a computer can determine the position of the absorption feature of interest as well as its absorption value. In this manner, the corresponding concentration of molecules of interest in the sample can be calculated. In addition, the wavelength corresponding to the current value where the absorption feature is centered can automatically be determined.

According to the scanning technique, the position of the absorption peak can be determined either by visual inspection of the absorption data, or where automated data analysis is required, by the use of algorithms. However, the usual current scanning technique is not fully satisfactory since it is completely passive in nature. That is, this technique relies entirely on the size of the current/wavelength scan region being large enough so that the wavelength of the desired absorption feature lies within the scan region and cannot drift so much that it misses the absorption feature altogether.

Several techniques have been used to compensate for the passive nature of the current scanning technique. For example, Fried et al (Applied Optics, Vol. 30(15), pp. 1916-1932 (1991)) discloses a reference spectrum to compensate for the effect of drift of the diode laser wavelength. According to the Fried et al technique, a reference spectrum is obtained corresponding to each sample spectrum by splitting the laser beam into several portions and passing one portion through the sample of interest and another through a dedicated cell containing a reference gas. After a data collection session is completed, the reference spectra are adjusted so that the same absorption peaks always occur at the same position. The same adjustment is then applied to the corresponding sample spectra. This technique is obviously not real-time and it does not change the diode laser output, but only the spectra. The purpose of this technique appears to be the enablement of subsequent spectra averaging so as to achieve an improvement in sensitivity, rather than to dynamically correct the diode laser output.

A second related technique is described by R. D. May, Rev. Sci. Instrum., 63(5), pp. 2922-2926 (1992). This technique is a real-time, active adjustment of the diode laser scans, based upon the calculation of autocorrelation of subsequent spectra. The autocorrelation is zero when the spectra are precisely aligned and non-zero values of the autocorrelation are used to calculated suitable adjustments to the diode laser scan in order to compensate for drift in the diode output wavelength. The drawback of this method is that the autocorrelation function calculation is complex. In the above publication, the calculation is carried out by using a Fast Fourier Transform and adding an array processor to the computer used to control the diode system. Unfortunately, array processors are expensive. The cost of an array processor represents a significant fraction (5–20%) of the cost of a complete diode laser control system.

To overcome the disadvantages of the prior art, it is an object of the present invention to provide a novel method for stabilization of wavelength in a laser spectrometer system, which includes scanning of the laser current or voltage signal and automatically correcting the scan for wavelength drift without the need for onerous and expensive additional computation. The inventive method allows for the wavelength corresponding to an absorption feature of interest to be automatically corrected in real time, and at the same time provides information relating to wavelengths immediately surrounding the absorption feature of interest, thereby serving system diagnostic purposes.

SUMMARY OF THE INVENTION

According to a first aspect of the present invention, a method for wavelength stabilization in a laser spectrometer useful in spectroscopic measurement is provided. The method comprises the following steps.

(a) An initial scan is performed which comprises applying a current or voltage signal to a laser. The current or voltage signal value is increased incrementally from a minimum signal value to a maximum signal value over a predetermined total number of signal values. The minimum and maximum signal values are selected such that an absorption feature of a species to be measured falls within the scan bounded by the minimum and the maximum signal values; (b) The relative position of the absorption feature is determined with respect to the applied signal values in the previous scan by analysis of detector outputs corresponding to the signal values in the previous scan; (c) An absorption value corresponding to the absorption feature is determined; (d) The concentration of the species to be measured is optionally calculated; (e) A new signal scan is defined by resetting the signal values from the previous scan, so as to set the absorption feature in the new signal scan in the same relative position with respect to the applied signal values as in the previous scan; (f) An additional scan is performed; and (g) Steps (b) through (f) are repeated until completion of the spectroscopic measurement.

According to a second aspect of the invention, in step (e) a new signal scan is defined when the relative position of the absorption feature with respect to the applied signal values exceeds a predetermined setpoint.

Third and fourth aspects of the invention are similar to those described above, except the laser spectrometer is specifically, a diode laser spectrometer, and the scanning is accomplished by varying diode laser current.

DETAILED DESCRIPTION OF THE PREFERRED EMBODIMENTS OF THE INVENTION

According to the present invention, the inventive method allows for stabilization of wavelength in a laser spectrometer system. Such systems have applicability in the detection and measurement of molecular gas phase species concentrations, and comprise a light source and a detector in optical communication with a sample region.

As used herein, the term "molecular gas phase species" refers to a molecular gas or vapor species which is the object of the absorption spectroscopy measurement.

Any molecular species of interest can be detected, subject only to the availability of a suitable light source. For example, water vapor, nitric oxide, carbon monoxide and methane or other hydrocarbons can be detected by measuring the attenuation of light from a diode laser source which emits light of a wavelength characteristic of the species.

Laser light sources which emit light in spectral regions where the molecules of interest absorb most strongly lead to improvements in measurement sensitivity. In particular, light sources which emit at wavelengths longer than about 2 µm are preferred, since many of the molecular species of interest have strong absorption bands in this region.

Any suitable wavelength-tunable light source can be used. In such light sources, the emission wavelength is controlled by application of an electrical signal, such as a current or voltage signal. Of the currently available light sources, diode laser light sources are preferred because of their narrow linewidth (less than about $10^{-3} cm^{-1}$) and relatively high intensity (about 0.1 to several milliwatts) at the emission wavelength.

Examples of diode lasers include Pb-salt and GaAs-type diode lasers. The Pb-salt-type laser requires cryogenic temperatures for operation and emits infrared light (i.e., wavelength greater than 3 µm), while the GaAs-type diode laser can operate at close to room temperature and emits in the near infrared region (0.8–2 µm).

Recently, diode lasers which include Sb in addition to GaAs (or other pairs of III–V compounds such as AsP) have been described (see, "Mid-infrared wavelengths enhance trace gas sensing," R. Martinelli, Laser Focus World, March 1996, p. 77). These diodes emit light of a wavelength greater than 2 µm while operating at −87.8° C. While such a low temperature is not convenient, it compares favorably with the cryogenic temperatures (less than −170° C.) required by Pb-salt lasers. Operation of similar lasers at 4 µm and 12° C. has also been reported (see, Lasers and Optronics, March 1996). Diode lasers of the above described type will most preferably operate at temperatures of at least −40° C. Use of a thermoelectric cooler for temperature control at such temperatures makes these light sources less complicated than the lower temperature diode systems. To make use of these lasers more desirable, improvement in the optical properties over current levels is important. For example, single mode diodes (i.e., diodes whose emission at fixed temperature and drive current is at a single wavelength with emission at other wavelengths at least 40 dB less intense) should be available.

Suitable light sources for use in the invention are not limited to the above described diode lasers. For example, other types of lasers which are similarly sized and tunable by simple electrical means, such as fiber lasers and quantum cascade lasers, are envisioned. The use of such lasers as they become commercially available is envisioned.

Stabilization of the laser spectrometer system is accomplished by first performing an initial scan which includes applying a current or voltage signal to the laser. The current or voltage signal value is increased incrementally from a minimum signal value to a maximum signal value over a predetermined total number of signal values. The minimum and maximum signal values are selected such that an absorption feature of a species to be measured falls within the scan bounded by the minimum and the maximum signal values.

Next, the relative position of the absorption feature is determined with respect to the applied signal values in the previous scan by analysis of detector outputs corresponding to the signal values in the previous scan. The absorption value corresponding to the absorption feature is then determined. The absorption value may be determined directly or by using harmonic detection techniques. Such techniques are described in copending applications Ser. No. 08/711,646, filed on even date herewith, Attorney Docket No. 016499-203, Ser. No. 08/711,504. filed on even date herewith, Attorney Docket No. 016499-204 and Ser. No. 08/711,781, filed on even date herewith, Attorney Docket No. 016499-206, which are hereby incorporated by reference.

The concentration of the species to be measured can optionally be calculated, and a new current or voltage signal scan is then determined by resetting the signal values from the previous scan, so as to set the absorption feature in the new signal scan in the same relative position with respect to the applied signal values as in the previous scan. Timing of the resetting step can alternatively depend on the drifting of the absorption feature beyond a setpoint. An additional scan is next performed, and the steps can be repeated until completion of the spectroscopic measurement. Note that the principal computations which are performed, namely determination of the position and size of the absorption feature, are required in any case to calculate the concentration of the species of interest. Thus, the present technique is very fast and simple.

As described above, the inventive method can be practiced by applying a current signal or a voltage signal to a light source, depending on the type of light source used. Although the following description of the invention has been written in terms of light sources having their emission wavelength controlled by current signal, it applies equally to light sources in which wavelength is controlled by applying a voltage signal.

The current signal applied to the laser is computer controlled and is scanned. That is, it is varied from a minimum to a maximum value for a predefined total number of current signal values. As used herein, the term "scan" refers to one cycle of current variation from a minimum to a maximum value.

The current signal values, and thus the increments between the current signal values, are also predefined, and can be determined by any number of mathematical relationships. Each current signal scan consists of a fixed total number of current signal values N, such that a given laser current signal corresponding to each point can be determined by an equation such as that shown below as Formula (I):

$$I(n) = I(1) + \left( \frac{n-1}{N-1} \right) i \qquad (I)$$

where I is the applied current signal for a particular scan point n which varies from 1 to N, and i is the maximum current signal minus the minimum current signal in the scan.

The individual current signals in the scan defined by the above equation have a linear relationship, with current signals varying from a minimum value at i(1), to a maximum value at I(1)+i. However, other scan shapes are also contemplated by the invention. For example, sinusoidal, exponential and arbitrary shapes which can be designed, for example, to give a more perfectly linear wavelength variation in the laser output can also be used.

The scan current signal range is preferably 2–40, and more preferably 3–20, times the width of the absorption feature, which depends on the temperature and pressure of the sample, as well as the species of interest. The total number of scan points N is preferably 30–700, and more preferably, 50–512.

An absorption feature of the molecular species which is the object of the measurement is initially set to fall within the minimum and maximum current signal values. It is preferable that the desired absorption feature is positioned at the center current signal value in the case an odd number of total current signal values is selected, or at one of the two center values for an even number of total current signal values.

The scan is preferably repeated with a frequency of at least 1 Hz, and more preferably with a frequency of from about 10 Hz to 10 kHz.

As the scan is initially set, the absorption feature should be centered at a current signal value, for example, at n=m[old], where m[old] is preferably a center scan point. During each scan, an output is generated by the detector corresponding to each current signal value. The outputs from the detector are stored in an array of N points, corresponding to the total number of current signal values N. Each output is then analyzed by an algorithm which determines that current signal value and scan point (n=m[new]) in the scan which corresponds to the center of the absorption feature. The corresponding absorption value and, optionally, the corresponding concentration of the species of interest are also determined.

The scan rate should be sufficiently slow to allow the computations to be performed prior to collecting data for the next scan. In general, a computer based on a 486-type or equivalent processor should have sufficient speed to accommodate current signal scan rates of about 10 Hz.

According to the inventive method, the value m can be used to reset the minimum current signal value I(1) from its previous value I(1)[old] to a new value I(1)[new], such that the absorption feature remains at the same point in the scan relative to the other values as in the previous scan and performing an additional scan. Thus, according to the above equation, I(1) is reset according to the following equation II:

$$I(1)[new]=I(1)[old]-(m[new]-m[old])i/N \qquad (II)$$

In practice, it may be impractical to reset I(1) after every scan. This is particularly true if the scan rate is relatively fast, for example, where the scan rate is about 10 Hz or greater, or where the function describing the scan is complex. In such cases, the time to reset I(1) and generate a new set of current signal scan values may be greater than the time for a single scan. However, the drift in laser properties over a period of seconds or minutes is generally small enough such that there is no danger that the absorption feature will drift outside of the range of current signal values in the scan.

Persons of ordinary skill in the art can readily appreciate that this resetting procedure can also be applied after a certain number of scans, as opposed to after every scan. Alternatively, the resetting procedure can be applied after a predefined amount of time. For example, if the size of the scan is two to three times the width of the absorption feature, resetting the scan one time per minute should be adequate.

In a further embodiment of the invention, a set point may be established for the relative position m of the absorption feature. As soon as the position, m of the absorption feature reaches or extends beyond this set point, the value of I(1) may be reset. Thus, dangerous drifts in the position of the absorption feature can be prevented by monitoring the value of m, corresponding to the absorption feature.

For example, a set point of 20% of the scan size from the minimum or maximum current value of the scan (i.e., m/N<0.2i or m/N>0.8i) can be used. Where the wavelength scan is initially set such that the absorption feature occurs at the center current signal value, and the size of the scan is about ten times the width of the absorption feature, the value of m can be checked after each scan. Thus, if the absorption feature reaches or exceeds the set values, then I(1) is reset according to the above equation. Otherwise I(1) and the entire current signal scan remain unchanged.

The inventive method has particular applicability in the detection of gas phase molecular species in a semiconductor processing system. Typical semiconductor processing systems include a processing chamber containing a semiconductor substrate on a substrate holder. A gas inlet is provided for delivering a process gas or plural gases to the processing chamber. Effluent from the processing chamber is exhausted through an exhaust line connected, for example, to a gas scrubber system.

The processes often call for reactive or nonreactive (inert) gas species which can be in a plasma- or non-plasma state. Examples of reactive gases which can be used include $SiH_4$, HCl and $Cl_2$, provided the moisture level is less than 1000 ppm. However, the reactive gases are not limited to these. Any inert gas such as, e.g., $O_2$, $N_2$, Ar and $H_2$ can be used.

In order to detect and measure the molecular gas phase species of interest, the laser spectroscopy system is placed in optical communication with a sample region, for example, in the processing chamber or the exhaust line of the semiconductor processing system.

While the invention has been described in detail with reference to specific embodiments thereof, it will be apparent to one skilled in the art that various changes and modifications can be made, and equivalents employed, without departing from the scope of the appended claims.

What is claimed is:

1. A method for wavelength stabilization in a diode laser spectrometer useful in spectroscopic measurement, comprising:

(a) performing an initial scan which comprises applying a current to a diode laser, wherein a current value is increased incrementally from a minimum current value to a maximum current value over a predetermined total number of current values, wherein the minimum and maximum current values are selected such that an absorption feature of a species to be measured falls within the initial scan bounded by the minimum and the maximum current values;

(b) determining the relative position of the absorption feature with respect to the applied current values in the previous scan in time of step (a) or step (f) by analysis of detector signals corresponding to the current values in the previous scan;

(c) determining an absorption signal corresponding to the absorption feature in the previous scan;

(d) optionally calculating the concentration of the species to be measured;

(e) defining a new current scan by resetting the current values from the previous scan, so as to set the absorption feature in the new current scan in the same relative position with respect to the applied current values as in the previous scan;

(f) performing an additional scan; and (g) repeating steps (b) through (f) until completion of the spectroscopic measurement.

2. The method for wavelength stabilization according to claim 1, wherein in step (d), the concentration is calculated after each scan.

3. The method for stabilizing wavelength according to claim 1, wherein in step (d), the concentration is calculated after averaging the absorption signal determined over a plurality of consecutive scans.

4. The method for stabilizing wavelength according to claim 1, wherein the species to be measured is water vapor, nitric oxide, carbon monoxide or methane.

5. The method for stabilizing wavelength according to claim 4, wherein the species to be measured is water vapor.

6. The method for stabilizing wavelength according to claim 1, wherein the diode laser spectrometer is used to detect a gas phase molecular species in a semiconductor processing system.

7. A method for wavelength stabilization in a diode laser spectrometer useful in spectroscopic measurement, comprising:

(a) performing an initial scan which comprises applying a current to a diode laser, wherein a current value is increased incrementally from a minimum current value to a maximum current value over a predetermined total number of current values, wherein the minimum and maximum current values are selected such that an absorption feature of a species to be measured falls within the initial scan bounded by the minimum and the maximum current values;

(b) determining the relative position of the absorption feature with respect to the applied current values in the previous scan in time of step (a) or step (f) by analysis of detector signals corresponding to the current values in the previous scan;

(c) determining an absorption signal corresponding to the absorption feature in the previous scan;

(d) optionally calculating the concentration of the species to be measured;

(e) defining a new current scan when the relative position of the absorption feature with respect to the applied current values exceeds a predetermined setpoint, by resetting the current values from the previous scan, so as to set the absorption feature in the new current scan in the same relative position with respect to the applied current values as in the previous scan;

(f) performing an additional scan; and (g) repeating steps (b) through (f) until completion of the spectroscopic measurement.

8. The method for wavelength stabilization according to claim 7, wherein in step (d), the concentration is calculated after each scan.

9. The method for stabilizing wavelength according to claim 7, wherein in step (d), the concentration is calculated after averaging the absorption signal determined over a plurality of consecutive scans.

10. The method for stabilizing wavelength according to claim 7, wherein the species to be measured is water vapor, nitric oxide, carbon monoxide or methane.

11. The method for stabilizing wavelength according to claim 10, wherein the species to be measured is water vapor.

12. The method for stabilizing wavelength according to claim 7, wherein the diode laser spectrometer is used to detect a gas phase molecular species in a semiconductor processing system.

13. A method for wavelength stabilization in a laser spectrometer useful in spectroscopic measurement, comprising:

(a) performing an initial scan which comprises applying a current or voltage signal to a laser, wherein a current or voltage signal value is increased incrementally from a minimum signal value to a maximum signal value over a predetermined total number of signal values, wherein the minimum and maximum signal values are selected such that an absorption feature of a species to be measured falls within the initial scan bounded by the minimum and the maximum signal values;

(b) determining the relative position of the absorption feature with respect to the applied signal values in the previous scan in time of step (a) or step (f) by analysis of detector outputs corresponding to the signal values in the previous scan;

(c) determining an absorption value corresponding to the absorption feature in the previous scan;

(d) optionally calculating the concentration of the species to be measured;

(e) defining a new current or voltage signal scan by resetting the signal values from the previous scan, so as to set the absorption feature in the new signal scan in the same relative position with respect to the applied signal values as in the previous scan;

(f) performing an additional scan; and (g) repeating steps (b) through (f) until completion of the spectroscopic measurement.

14. The method for wavelength stabilization according to claim 13, wherein in step (d), the concentration is calculated after each scan.

15. The method for stabilizing wavelength according to claim 13, wherein in step (d), the concentration is calculated after averaging the absorption signal determined over a plurality of consecutive scans.

16. The method for stabilizing wavelength according to claim 13, wherein the species to be measured is water vapor, nitric oxide, carbon monoxide or methane.

17. The method for stabilizing wavelength according to claim 16, wherein the species to be measured is water vapor.

18. The method for stabilizing wavelength according to claim 13, wherein the diode laser spectrometer is used to detect a gas phase molecular species in a semiconductor processing system.

19. A method for wavelength stabilization in a laser spectrometer useful in spectroscopic measurement, comprising:

(a) performing an initial scan which comprises applying a current or voltage signal to a laser, wherein a current or voltage signal value is increased incrementally from a minimum signal value to a maximum signal value over a predetermined total number of signal values, wherein the minimum and maximum signal values are selected such that an absorption feature of a species to be measured falls within the initial scan bounded by the minimum and the maximum signal values;

(b) determining the relative position of the absorption feature with respect to the applied signal values in the previous scan in time of step (a) or step (f) by analysis of detector outputs corresponding to the signal values in the previous scan;

(c) determining an absorption value corresponding to the absorption feature in the previous scan;

(d) optionally calculating the concentration of the species to be measured;

(e) defining a new current or voltage signal scan when the relative position of the absorption feature with respect to the applied current or voltage signal values exceeds a predetermined setpoint, by resetting the signal values from the previous scan, so as to set the absorption feature in the new signal scan in the same relative position with respect to the applied signal values as in the previous scan;

(f) performing an additional scan; and (g) repeating steps (b) through (f) until completion of the spectroscopic measurement.

20. The method for wavelength stabilization according to claim 19, wherein in step (d), the concentration is calculated after each scan.

21. The method for stabilizing wavelength according to claim 19, wherein in step (d), the concentration is calculated after averaging the absorption value determined over a plurality of consecutive scans.

22. The method for stabilizing wavelength according to claim 19, wherein the species to be measured is water vapor, nitric oxide, carbon monoxide or methane.

23. The method for stabilizing wavelength according to claim 22, wherein the species to be measured is water vapor.

24. The method for stabilizing wavelength according to claim 19, wherein the diode laser spectrometer is used to detect a gas phase molecular species in a semiconductor processing system.

* * * * *